United States Patent [19]
Allen et al.

[11] 4,233,035
[45] Nov. 11, 1980

[54] ADDITIVES FOR AVIATION AND SIMILAR FUELS

[75] Inventors: Edward A. Allen, Havant; Peter C. Phillips, Emsworth; Terence Smithson, Southsea, all of England

[73] Assignee: National Research Development Corporation, London, England

[21] Appl. No.: 924,718

[22] Filed: Jul. 14, 1978

Related U.S. Application Data

[63] Continuation of Ser. No. 777,684, Mar. 15, 1977, abandoned.

[30] Foreign Application Priority Data

Mar. 17, 1976 [GB] United Kingdom ............... 10834/76

[51] Int. Cl.$^2$ ................................................ C10L 1/22
[52] U.S. Cl. .......................................................... 44/73
[58] Field of Search ............................................. 44/73

[56] References Cited
U.S. PATENT DOCUMENTS 2,285,878   6/1942   White et al.

FOREIGN PATENT DOCUMENTS 861794   2/1961   United Kingdom .
940709   10/1963   United Kingdom .

*Primary Examiner*—Winston A. Douglas
*Assistant Examiner*—Y. Harris-Smith
*Attorney, Agent, or Firm*—Oblon, Fisher, Spivak, McClelland & Maier

[57] ABSTRACT

A hydrocarbon fuel, especially a copper-sweetened aviation jet fuel, contains a metal deactivator which is an oxime of either an orthohydroxy aromatic ketone or α-hydroxy aliphatic ketone, or an imine of a diamine with an ortho hydroxy aromatic ketone, an alkyl substituted ortho hydroxy aromatic aldehyde or a -diketone. Preferred materials include oximes of 2-hydroxy-5-t-butyl benzophenone and 2-hydroxy-5-nonyl acetophenene and di-imines of ethylene and propylene diamines with benzoyl acetone, 5-t-octylsalicylaldehye or 2-hydoroxy-5-methyl butyrophenone.

The metal de-activator is added in conventional proportions, typically about 5 to 10 ppm (by weight) to the fuel which may contain either conventional additives such as anti-static, anti-icing and corrosion inhibiting additives.

14 Claims, No Drawings

ADDITIVES FOR AVIATION AND SIMILAR FUELS

This is a continuation of application Ser. No. 777,684 filed Mar. 15, 1977 now abondoned.

The invention relates to organic compounds which are capable of chelating metals and may be used to improve the high temperature thermal stability of hydrocarbon fuels, especially aviation fuels.

Aviation fuels commonly contain metals such as iron, zinc and especially copper, picked up from reagents used in their production or from containers, pipelines etc. Concentrations of such metals as low as 0.1 parts per million adversely affect the high temperature stability of fuels, apparently by acting as oxidation and polymerisation catalysts. The high temperature stability of such metal containing fuels may be improved by the addition of so called metal de-activators which are generally metal-chelating organic compounds.

N.N'-disalicylidene-1,2-ethanediamine was formerly widely used as a metal de-activator but was found to produce sediment found to contain copper and iron. The propane analogue, NN'-disalicylidene-1,2-propane diamine forms more soluble complexes, but still produces precipitates in the presence of certain other desirable additives. There is therefore a need for metal de-activators which are effective in preventing high temperature oxidation and gum formation and which form metal chelates of high solubility in aviation, or other hydrocarbon fuels.

According to the present invention, a hydrocarbon fuel contains a metal de-activator which is:

A. an oxime having the formula

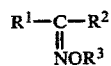

wherein $R^1$ represents an alkyl group or a benzenoid aromatic group, $R^2$ represents an orthohydroxy benzenoid aromatic group or an α-hydroxy group having the formula

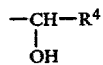

wherein $R^4$ represents an alkyl or benzenoid aromatic group; and $R^3$ represents a hydrogen atom or an alkyl group: or B. a ketimine of a β-diketone and a diamine and having the formula

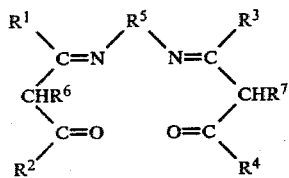

where $R^1$, $R^2$, $R^3$ & $R^4$ represent alkyl or benzenoid aromatic groups, $R^6$ & $R^7$ represent alkyl groups or hydrogen atoms and $R^5$ represents an alkylene group, a cycloalkylene group a benzenoid aromatic group or an alkyl substituted derivative thereof: or C. an imine of an ortho acyl phenol and a diamine and has the formula

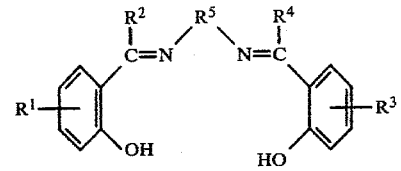

wherein $R^1$, $R^3$ represent alkyl groups, $R^2$, $R^4$ represent alkyl or benzenoid aromatic groups or hydrogen atoms and $R^5$ represents an alkylene group, a cycloalkylene group, a benzenoid aromatic group or an alkyl substituted derivative thereof. The term "benzenoid aromatic group" as used herein includes phenyl groups, substituted, especially alkyl substituted, phenyl groups, hydrocarbon polycyclic aromatic groups based on benzene and derivatives, especially alkyl substituted derivatives, of said polycyclic aromatic groups. The alkyl groups present in the metal de-activators of the present invention, either as groups $R^1$ to $R^5$ in the above formulae or as substituents in the benzenoid aromatic group, may be straight or branched chain alkyl groups and may vary in length over a wide range from $C_1$ to at least $C_{20}$. Whilst short chains of $C_1$ to $C_{10}$ will generally be easier to introduce, longer chains may be advantageous in increasing the solubility of the de-activator in the hydrocarbon fuel.

The metal de-activators will normally be added to the fuel in low concentrations typically 5 to 10 parts per million (by weight) although higher or lower concentrations may sometimes be desirable. They form complexes with the trace metals in the fuel and the solubility of these complexes in the particular fuel used governs the suitability of each de-activator for use in that fuel. The metal de-activators are especially advantageous in aviation fuels, such as AVTUR (Aviation turbine fuel similar to ASTMS specification JET A/1 or UK Defence Standard D. Eng. D. 2494) where copper is the predominant trace element. Hence for use in such fuels the de-activator should preferably form a copper complex having a solubility in the fuel, at room temperature, of at least 10 ppm and preferably at least 40 ppm by weight. This solubility may be influenced by other additives in the fuel and should therefore be verified on the actual fuel mix to be used.

Thus according to a first aspect of the present invention the metal de-activator is an oxime having the general formula in A. above. Preferred de-activators in accordance with this aspect of the invention include those in which $R^1$ represents an unsubstituted phenyl or alkyl group $R^2$ represents an ortho-hydroxy phenyl or alkyl substituted phenyl group, such as a 2-hydroxy-5-butyl phenyl or 2-hydroxy-5-nonyl phenyl group and $R^3$ represents a hydrogen atom and those in which $R^2$ represents an α-hydroxy alkyl group and $R^1$ and $R^4$ each represent a secondary alkyl group, such as a 1-ethyl 1-n-butyl methyl group. Especially suitable metal de-activators for AVTUR-type aviation fuels include 2-hydroxy-5-t-butyl benzophenone oxime and 2-hydroxy-5 nonyl acetophenone oxime.

Various routes for synthesis of the metal de-activators in accordance with this aspect of the present invention will be apparent to those skilled in the art, based on conventional oxime synthesis, and many of the compounds are commercially available, for example, as complexing reagents for metal extraction. Compounds which are α-hydroxy oximes ($R^2$ represents —CHOH- $R^4$) may typically be synthesised by the following route:

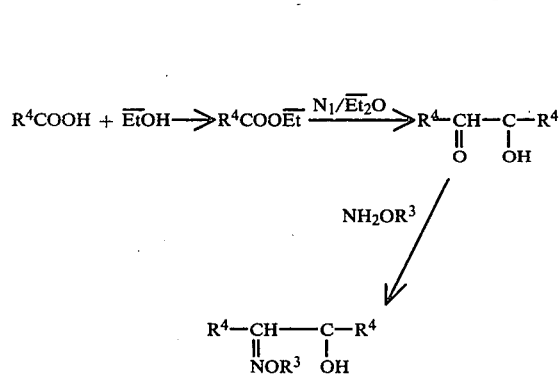

Those compounds which are oximes of ortho acyl phenols including o-hydroxy phenones ($R^1$ represents an alkyl or benzenoid aromatic group and $R^2$ represents an ortho-hydroxy phenyl or alkyl substituted phenyl group may typically be prepared by the route:

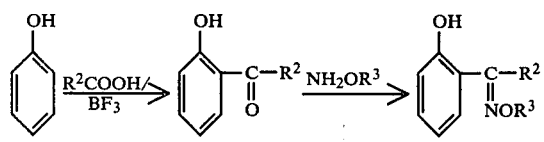

Alternatively the intermediate ketone may be prepared by Fries re-arrangement, preferably photochemical, of an ester as follows:

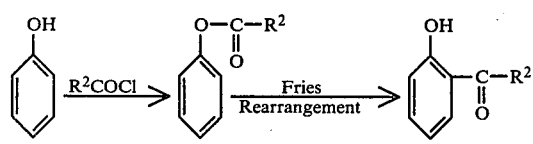

It will be apparent that substituted phenols may be employed leading to correspondingly substituted o-hydroxy phenones.

According to a second aspect of the invention, the metal de-activator is a ketimine having the general formula in B. above, preferably where $R^1$, $R^2$, $R^3$ and $R^4$ represent alkyl, phenyl or alkyl substituted phenyl groups and $R^1$ and $R^2$ are identical to $R^3$ and $R^4$ respectively. $R^5$ is preferably an ethylene group $-(CH_2)_2$ or a methyl substituted ethylene group $-CH_2-CH(CH_3)$.

Especially suitable metal de-activators for AVTUR-type aviation fuels include bis-benzoylacetone propylene diamine ($R^1=R^3=CH:R^2=R^4=$phenyl; $R^5=-CH_2-CH(CH_3)$).

The ketimine used as metal de-activations in accordance with this aspect of the present invention may be prepared by standard routes for ketimine (Schiff's base) production as well known to those skilled in the art. For example, the diketone and diamine may be condensed together by co-solution in a suitable solvent such as ethanol

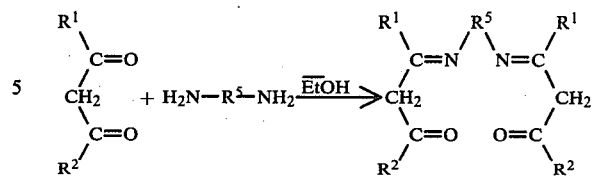

According to the third aspect of the present invention the metal de-activator is an imine of a substituted ortho-acyl phenol having the general formula in C. above. It has been found that ketimines of certain substituted ortho-acyl phenols are at least as effective as metal-deactivators as those derived from salicylaldehyde and form more soluble copper complexes. Preferred compounds are those in which $R^1$ and $R^3$ both represent an alkyl group containing at least 6 carbon atoms, preferably in a non-linear arrangement, or $R^2$ and $R^4$ both represent an alkyl group having at least 2 carbon atoms. Especially suitable metal de-activators for AVTUR-type aviation fuels include $NN^1$ di(5-t-octylsalicylidene) ethylene diamine and $NN^1$ bis(2-hydroxy-5-methyl-butyrophenone) ethylene diamine.

The imines of substituted salicylaldehydes may be prepared by the same routes as those of $\beta$-diketones as described above. For example, the ortho acyl phenol and the diamine may be condensed together by co-solution in a suitable solvent, such as ethanol.

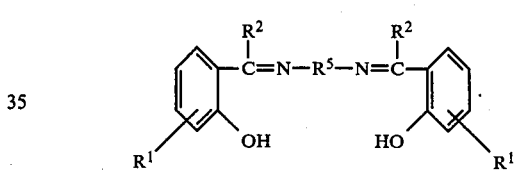

The ortho acyl phenols may in some cases be prepared by reduction of a substituted salicyclic acid according to the scheme

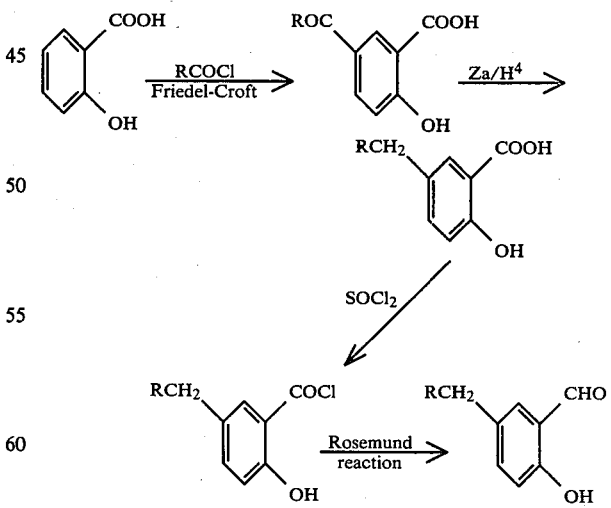

wherein $RCH_2=R^1$.

Alternatively they may be prepared by direct formylation of a substituted phenol using 1,1 dichlorodimethyl ether/titanium tetrachloride as the reagent

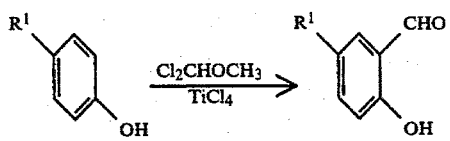

The ketones may be prepared by reacting a p-substituted phenol with an aliphatic carboxylic acid using boron trifluoride to catalyse both the esterification and the re-arrangement of the resulting ester.

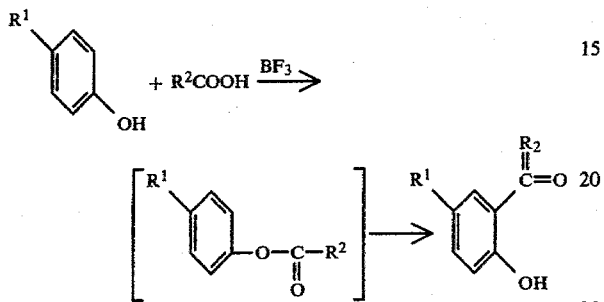

The preparation, testing and incorporation into fuels of specific metal de-activators in accordance with the present invention will now be described by way of example only.

EXAMPLE 1

2-hydroxy-5-t-butyl benzophenone oxime was prepared as follows: 5-tert butyl phenol (9.2 g) and benzoic acid (10 g) were co-dissolved in tetrachloroethane (50 cm$^3$). Boron trifluoride (10 g) was passed into the solution after which the mixture was heated for 5 hours at 100° C., and then poured into 10% aqueous sodium hydroxide (500 cm$^3$). The organic layer was separated and the solvent removed by steam distillation leaving crude 2-hydroxy-5-tertbutyl benzophenone which was purified by distillation. 2-hydroxy-5-tertbutyl benzophenone (25.4 g) (prepared as above), hydroxylamine hydrochloride (13.9 g), ethanol (75 cm$^3$) and pyridine (75 cm$^3$) were mixed together and refluxed for 3 hours, after cooling the mixture was poured into water and extracted with ether. The ether extract was washed with dilute hydrochloric acid and water, dried and evaporated. The residual oil was distilled under vacuum to give 2-hydroxy-5-tertbutyl benzophenone oxime (14.2 g).

The product, when analysed by thermogravimetric techniques showed that it decomposed at 196° to 204° C. It showed no reaction detectable by UV spectroscopy when heated at 90° C. for 1 hour with either of two common aviation fuel additives, a fuel system icing inhibitor (FSII comprising ethylene glycol monomethyl ether) or HITEC E515 (a corrosion/wear inhibitor comprising dilinoleic acid and diamyl phenol acid phosphate in a kerosene-based hydrocarbon solvent).

The copper complex was prepared by reacting the hydroxy oxime with excess cupric acetate in ethanol solution. It was obtained as a green solid which decomposed at 265° to 270° C.

A saturated solution of the copper complex was prepared under nitrogen in AVTUR aviation fuel which had been percollated through Fuller's earth to reduce its acidity to 0.003 mg KOH/g. The solution was filtered at 20° C. through a "Millipore" membrane filter of pore size 0.45 μm ("Millipore" is a trade mark) and the copper concentration determined by atomic absorption without exposing the solution to the air at any stage. The solubility corresponded to greater than 300 ppm (w/w) of copper.

The original 2-hydroxy-5-t-butyl benzophenone oxime was incorporated into samples of a blended AVTUR fuel containing anti-static additive (ASA-3-containing electrically conducting chromium salts-supplied by Shell Chemical Co) at 0.5 ppm (by weight), FSII at 0.15% (v/v) and HITEC E515 at 14.3 mg/l.

Samples of
a. the blended fuel only
b. the blended fuel plus added copper (as copper naphthenate)
c. the blended fuel plus metal de-activator and
d. the blended fuel plus metal de-activator plus added copper. were compared for conductivity (IP 274) Water Reaction (IP 289) Water Separometer Index Modified (WSIM-ASTMS D 2550) and Thermal Oxidation Stability (JFTOT - IP 323) by methods as described in UK Defence Specification D Eng D2497 (Issue No 7). The results are shown in the Table.

EXAMPLE 2

Benzoylacetone (81 g) was reacted with propylene diamine (18.5 g) by boiling in ethanol (100 cm$^3$) for 15 minutes and then allowing the solution to stand overnight. The crude product was obtained as a hard crystalline mass. It was purified twice by recrystallisation from ethanol to give analytically pure bisbenzoylacetone propylene diamine (56.2 g) m.pt 116°–118° C. as white crystals.

Bis(benzoylacetone) propylene diamine was examined by thermogravimetric analysis and found to decompose at 290°–291° C.

The copper complex was prepared by reacting the ketimine with cupric acetate (as in Ex 1) and had a solubility in deacidified AVTUR of more than 200 ppm by weight of Cu (after filtration as in Example 1).

The original bis benzoylacetone propylene diamine was incorporated into blended AVTUR and tested as described in Example 1. The results are shown in the table.

EXAMPLE 3

5-octylsalicylaldehyde was prepared as follows: p-octyl phenol (20.6 g) was dissolved in dry methylene chloride (400 cm$^3$). The solution was cooled in an ice bath, stirred and treated carefully with titanium tetrachloride (44 cm$^3$). 1,1-Dichloromethyl methyl ether (30 cm$^3$) was then added dropwise to the cooled stirred solution. After the addition was complete, the temperature was raised to 40° C. and stirring continued for a further 15 minutes. The mixture was then poured into crushed ice (500 g) and the organic layer extracted with ether. The ethereal solution was washed several times with water, dried over anhydrous sodium sulpate and evaporated. The oily residue was purified by fractional distillation under vacuum to give 5-octylsalicylaldehyde as a colourless liquid which solidified at 30° C.

NN$^1$-di(5-octylsalicylidene) ethylene diamine was prepared by codissolving stoichiometric quantities of 5-octylsalicylaldehyde (prepared as described above) and ethylene diamine in hot absolute alcohol. After heating for 15 minutes the mixture was cooled to precipitate the Schiff's base (ketimine) in the form of yellow plates m p 157°–158° C.

The copper complex of the Schiff's base was prepared by reacting it with excess cupric acetate in ethanol solution. It had a solubility in deacidified AVTUR at 20° C. of greater than 90 ppm by weight of Cu (after filtration as in Example 1).

The original ketimine was incorporated into blended AVTUR are tested as in Example 1. The results are shown in the table.

EXAMPLE 4

N,N¹ bis(2 hydroxy-5-methyl butyrophenone) ethylene diamine (N,N¹ bis(2-hydroxy-5-methyl-α-propyl benzylidene)diaminoethane) was prepared by co-dissolving stoichiometric quantities of propyl (2-hydroxy-5-methylphenol) ketone and ethylene diamine in ethanol, heating the solution to boiling, under reflux, for 15 minutes and then allowing to cool. The ketimine (Schiff's base) crystallised out as yellow needles, m.pt 166°–168° C. (after recrystallisation from ethanol/benzene).

The copper complex was prepared as a brown solid which decomposed at 290° C. and had a solubility in deacidified AVTUR at 20° C. of greater than 60 ppm by weight of Cu (after filtration as in Example 1).

The original ketimine was incorporated into blended AVTUR and tested as in Example 1. The results are shown in the Table.

EXAMPLE 5

2-hydroxy-5-nonyl acetophenone oxime was obtained as a an impure solution in a hydrocarbon type diluent under the trade name "Shell Metal Extractant 529" ("Shell" is a Trade Mark) and was purified by vacuum distillation followed by treatment with hydroxylamine to reconstitute the partially degraded oxime. An alternative purification involves absorption on silica, elution with methanol, extraction of the copper complex from chloroform into water and chromatography of the copper complex on silica with hexane as eluant.

It was incorporated into blended AVTUR and tested as in Example 1. The results are shown in the Table.

TABLE

| Metal Deactivator Compound | Added ppm (w/w) | Copper ppm | Conductivity pS/meter | Water Reaction Temp °F. | Interface[1] | Separation[2] | WSIM | Thermal Stability (JFTOT) 500° F. pressure drop,ins Hg | Tube[3] deposit | 540° F. pressure drop,ins Hg | Tube[3] deposit |
|---|---|---|---|---|---|---|---|---|---|---|---|
| None | | None | 90 | 56 | 1b | 2 | 62 | Nil | 1 | — | — |
| None | | 0.15 | 200 | 60 | 1b | 2 | 59 | Nil | 2A | 0.05 | 3A |
| 2-hydroxy-5-t-butyl benzophenone oxime | 5 | None | 290 | 71 | 1b | 2 | 56 | Nil | 1 | 0.08 | 1 |
| 2-hydroxy-5-t-butyl benzophenone oxime | 10 | None | 210 | 59 | 1b | 2 | 52 | — | — | — | — |
| 2-hydroxy-5-t-butyl benzophenone oxime | 5 | 0.15 | 300 | 65.6 | 1b | 2 | 58 | Nil | 1 | Nil | 1 |
| Bis(benzoylacetone) propylene diamine | 5 | None | 230 | 67.5 | 1b | 2 | 58 | Nil | 1 | Nil | 1 |
| Bis(benzoylacetone) propylene diamine | 5 | 0.15 | 190 | 68.5 | 1b | 2 | 61 | Nil | 1 | Nil | 1 |
| NN¹-di(5-t-octyl[4] salicylidene) ethylene diamine | 5 | None | 230 | 71 | 1b | 2 | 63 | Nil | 1 | Nil | 1 |
| NN¹-di(5-t-octyl[4] salicylidene) ethylene diamine | 5 | 0.15 | 230 | 70 | 1b | 2 | 57 | Nil | 1 | Nil | 1 |
| Bis(2-hydroxy-5-methyl butyrophenone) ethylene diamine | 5 | None | 180 | 70 | 1b | 2 | 61 | Nil | 1 | Nil | 1 |
| Bis(2-hydroxy-5-methyl butyrophenone) ethylene diamine | 5 | 0.15 | 200 | 70 | 1b | 2 | 60 | Nil | 1 | Nil | 1 |
| 2-hydroxy-5-nonyl acetophenone oxime | 5 | None | 150 | 63.2 | 1b | 2 | 50 | Nil | 1 | — | — |
| 2-hydroxy-5-nonyl acetophenone oxime | 5 | 0.15 | 150 | 62.4 | 1b | 2 | 57 | Nil | 1 | — | — |

NOTES:
[1] 1b = small clear bubbles not more than 50% of the surface, no shreds lace or film at interface (pass test).
[2] 2 = absence of emulsions and/or precipitates within or upon either layer excepting small air bubbles or small water droplets that may be observed in fuel layer (pass test).
[3] Number indicates amount of deposit (maximum permissible = 3) "A" denotes blue deposit (fails test).
[4] t-octyl = 1,1,3,3 tetramethyl butyl.

We claim:

1. A hydrocarbon fuel containing a metal de-activator which is a hydroxy oxime having the formula

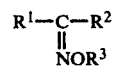

wherein $R^1$ represents an alkyl group or a benzenoid aromatic group, $R^2$ represents an orthohydroxy benzenoid aromatic group or an α-hydroxy group having the formula

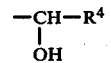

wherein $R^4$ represents an alkyl or benzenoid aromatic group; and $R^3$ represents a hydrogen atom or an alkyl group.

2. A hydrocarbon fuel according to claim 1 containing 5 to 10 parts per million by weight of the metal deactivator.

3. A hydrocarbon fuel according to claim 1 wherein the metal de-activator is a hydroxy oxime having the formula

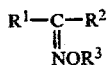

wherein $R^1$ represents group selected from alkyl, phenyl and alkyl substituted phenyl groups; $R^2$ represents a group selected from ortho-hydroxy phenyl, and alkyl substituted ortho-hydroxy phenyl groups and $R^3$ represents a hydrogen atom.

4. A hydrocarbon fuel according to claim 3 wherein the metal de-activator is 2-hydroxy-5-t-butyl benzophenone oxime.

5. A hydrocarbon fuel according to claim 3 wherein the metal de-activator is 2-hydroxy-5-nonyl acetophenone oxime.

6. A hydrocarbon fuel according to claim 1 wherein the metal de-activator is a ketimine of a $\beta$-diketone and a diamine having the formula

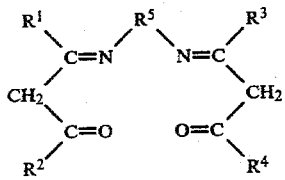

wherein $R^1$ and $R^3$ are the same or different and each represents a group selected from alkyl, phenyl and alkyl substituted phenyl groups, $R^2$ and $R^4$ are the same or different and each represents a group selected from the group consisting of phenyl and alkyl substituted phenyl groups, and $R^5$ represents a group selected from straight and branched chain alkylene groups.

7. A hydrocarbon fuel according to claim 6 wherein $R^1$ and $R^2$ are identical to $R^3$ and $R^4$ respectively.

8. A hydrocarbon fuel according to claim 6 wherein $R^5$ represents a group selected from ethylene and methyl substituted ethylene groups.

9. A hydrocarbon fuel according to claim 6 wherein the metal de-activator is bis(benzoylacetone)propylene diamine.

10. A hydrocarbon fuel according to claim 1 wherein the metal de-activator is $NN^1$ di(5-t-octyl-salicylidene)ethylene diamine.

11. A hydrocarbon fuel containing a metal de-activator which is a ketimine of a $\beta$-diketone and a diamine having the formula

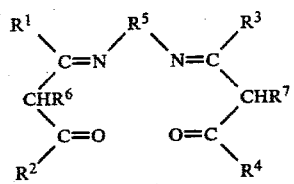

wherein $R^1$ and $R^3$ represent alkyl or benzenoid aromatic groups, $R^2$ and $R^4$ represent phenyl or alkyl substituted phenyl groups, $R^6$ and $R^7$ represent alkyl groups or hydrogen atoms and $R^5$ represents an alkylene group, a cycloalkylene group, a benzenoid aromatic group, or an alkyl substituted derivative thereof.

12. A hydrocarbon fuel containing a metal de-activator which is a di-imine of a substituted salicylaldehyde and a diamine having the formula

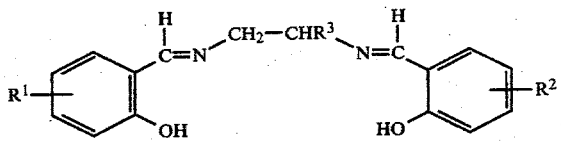

wherein $R^1$ and $R^2$ represent alkyl groups containing from 6 to 20 carbon atoms and $R^3$ represents a hydrogen atom or a methyl group.

13. The hydrocarbon fuel of claim 11 containing 5 to 10 parts per million by weight of said metal de-activator.

14. The hydrocarbon fuel of claim 12 containing 5 to 10 parts per million by weight of said metal de-activator.

* * * * *

UNITED STATES PATENT AND TRADEMARK OFFICE
CERTIFICATE OF CORRECTION

PATENT NO. : 4,233,035
DATED : November 11, 1980
INVENTOR(S) : Edward A. Allen et al It is certified that error appears in the above—identified patent and that said Letters Patent is hereby corrected as shown below:

In Claim 6, line 1, "claim 1" should read --claim 11--.

In Claim 10, line 1, "claim 1" should read --claim 12--.

Signed and Sealed this

Twenty-eighth Day of April 1981

[SEAL]

Attest:

RENE D. TEGTMEYER

Attesting Officer — Acting Commissioner of Patents and Trademarks